United States Patent [19]

Makisumi et al.

[11] 4,200,757
[45] Apr. 29, 1980

[54] PROCESS FOR THE PRODUCTION OF 3-AMINOISOXAZOLES

[75] Inventors: Yasuo Makisumi, Kawanishi; Akira Murabayashi, Ibaraki; Takashi Sasatani, Sakai, all of Japan

[73] Assignee: Shionogi & Co., Ltd., Osaka, Japan

[21] Appl. No.: 912,252

[22] Filed: Jun. 5, 1978

[30] Foreign Application Priority Data

Jun. 8, 1977 [JP] Japan .................................. 52-68173

[51] Int. Cl.$^2$ .......................................... C07D 261/08
[52] U.S. Cl. .................................................... 548/246
[58] Field of Search ..................................... 260/307 H

[56] References Cited

U.S. PATENT DOCUMENTS 3,242,189  3/1966  Bretschneider et al. ......... 260/307 H

OTHER PUBLICATIONS

Matsumura et al., "J. Takeda Res. Lab.," vol. 30, No. 3, (1971), pp. 475–492.
Weissberger–"The Chemistry of Heterocyclic Compounds," vol. 17 (1962), Interscience Publ., pp. 9–10.
Migrdichian–"The Chemistry of Organic Cyanogen Compounds,"–(1947)–Reinhold Publ.–pp. 84, 94.
Okeda et al.–Yakugaku Zasshi, 76, 66–67 (1956).

Primary Examiner—Anton H. Sutto
Attorney, Agent, or Firm—Wenderoth, Lind & Ponack

[57] ABSTRACT

3-Aminoisoxazoles of the formula:

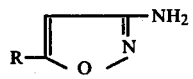

(wherein R is $C_1$–$C_6$ alkyl, phenyl or halo-phenyl) are prepared by reacting a $\beta$-ketonitrile of the formula:

R—CO—CH$_2$CN (wherein R is as defined above) with a compound of the formula:

HY (wherein Y is $C_1$–$C_6$ alkoxy or $C_1$–$C_6$ alkylthio) in the presence of an acid in a solvent to give an iminium salt of the formula:

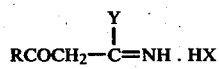

(wherein X is the residue of said acid; R and Y are each as defined above) and further reacting the iminium salt with hydroxylamine in an inert solvent.

4 Claims, No Drawings

PROCESS FOR THE PRODUCTION OF 3-AMINOISOXAZOLES

The present invention relates to a process for the production of 3-aminoisoxazoles.

The following processes for the production of 3-aminoisoxazoles have been heretofore known:
(1) Iwai et al., Chem. Pharm. Bull., 14, 1277–1286 (1966)
(2) Hoffmann-La Roche, Japanese Patent Publication No. 21147/1966 (corresponding to U.S. Pat. No. 3,242,189)
(3) Matsumura et al., J. Takeda. Res. Lab., 30, 475 (1971)
(4) Okeda et al., Yakugaku Zasshi, 76, 66 (1956)

These known processes, however, have the following weak points and are not altogether satisfactory for industrial preparation: (a) isomeric 5-aminoisoxazoles are always produced as by-products along with 3-aminoisoxazoles; (b) 5-aminoisoxazoles are usually produced as main products; (c) even if 3-aminoisoxazoles are produced as main products, the yield is not satisfactory; and (d) it is necessary to employ N-acylhydroxylamine as a rather special reactant for obtaining 3-aminoisoxazoles in a higher yield.

After diligent investigation of much improved processes for the production of 3-aminoisoxazoles free from above defects, the present inventors have succeeded in establishing the present invention.

According to the present invention, there is provided a process for the production of 3-aminoisoxazoles of the formula:

(wherein R is $C_1$–$C_6$ alkyl, phenyl or halo-phenyl) which process comprises reacting a β-ketonitrile of the formula:

R—CO—CH$_2$CN    (I)

(wherein R is as defined above) with a compound of the formula:

HY    (II)

(wherein Y is $C_1$–$C_6$ alkoxy or $C_1$–$C_6$ alkylthio) in the presence of an acid in a solvent to give an iminium salt of the formula:

(wherein X is the residue of said acid; R and Y are each as defined above) and further reacting the resulting iminium salt with hydroxylamine, preferably under basic conditions in an inert solvent.

The definitions of the above-mentioned substituent groups can be illustrated by the following description:

The alkyl includes methyl, ethyl, propyl, isopropyl, butyl, isobutyl, t-butyl, pentyl, isopentyl, and hexyl; the halo-phenyl includes o-chlorophenyl, p-chlorophenyl, o-bromophenyl and p-fluorophenyl; the alkoxy includes methoxy, ethoxy, propoxy, isopropoxy, isobutoxy, pentoxy and the like; the alkylthio includes methylthio, ethylthio, propylthio, isopropylthio, butylthio and the like.

The present chemical process can be shown in the following reaction scheme:

(First step)

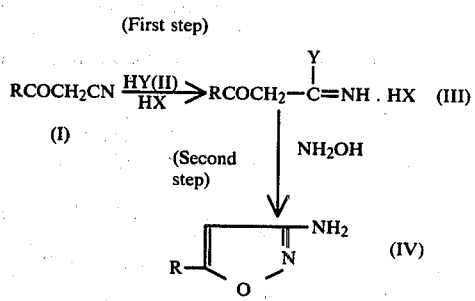

(wherein R, X and Y are each as defined above)

The first step can be carried out by reacting β-ketonitrile (I) with an alkanol or alkyl mercaptan (II) in the presence of an acid. Said alkanol or alkyl mercaptan (II) includes methanol, ethanol, isopropanol, isobutanol, methyl mercaptan, ethyl mercaptan, isopropyl mercaptan and the like. The acid includes hydrogen chloride, hydrogen bromide, sulfuric acid and the like. Such a reaction can be carried out according to the conventional process for converting nitriles into corresponding iminoethers in a suitable solvent (e.g. benzene, toluene, xylene, chloroform, methylene chloride) with cooling below room temperature.

The second step can be carried out by reacting the iminium salt (III) with hydroxylamine. This reaction can be effected by reacting the iminium salt (III) with hydroxylamine in the presence of a base in a suitable solvent and then the resulting oxime is subjected to ring closure by treating with an acid. The hydroxylamine is available in its salt forms such as hydroxylamine hydrochloride, hydroxylamine sulfate and the like. The base includes triethylamine, N-methylmorpholine and alkali alkoxide. The acid includes hydrochloric acid, sulfuric acid, acetic acid and the like. The solvent includes methanol, ethanol and the like. The reaction is ordinarily carried out below 100° C., preferably in the range of 40° to 80° C.

The second step can be generally considered to run as shown in the following reaction scheme:

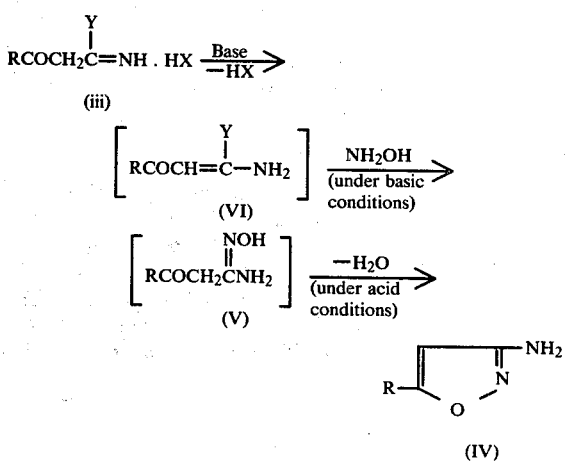

(wherein R, X and Y are each as defined above)

The industrial advantages of the present invention over prior art processes are as follows:

(1) 3-Aminoisoxazoles (IV) have been prepared in a high yield, by minimizing formation of by-products, 5-aminoisoxazoles, to selectively produce oximes (V) and then by subjecting those oximes (V) to ring closure with an acid. In contrast to known processes in which relatively large amounts of 5-amino isomers are produced, the process of this invention affords 5-amino isomers in only about 3 to 4% yield. It is a most favorable merit of this invention.

(2) The operation of the reaction is simple, and those two steps can be carried out continuously. Overall yield up to 95% can be easily attained.

(3) β-Ketonitrile (I) used as a reagent can be easily prepared from the corresponding methyl ketone via monochloromethyl ketone intermediate as follows:

RCOCH$_3$ $\xrightarrow{Cl_2}$ RCOCH$_2$Cl $\xrightarrow{NaCN}$ RCOCH$_2$CN   (I)

(wherein R is as defined above).

(4) A small amount of 5-aminoisoxazoles, produced as undesirable by-products, can be easily removed as an acid material, after being hydrolyzed into isoxazole-5-ones (VII) in the ring closure treatment as shown in the following reaction scheme. Accordingly, the objective products (IV) can be isolated in a high purity.

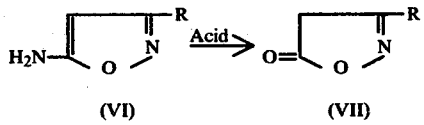

(VI)                    (VII)

(wherein R is as defined above).

(5) Thus obtained 3-aminoisoxazoles (IV), for example, 3-amino-5-t-butylisoxazole (IVa), can be converted into 1,1-dimethyl-3-(5-t-butyl-3-isoxazolyl)urea (VIII), which is available as a potent and selective herbicide, by reacting with N,N-dimethylcarbamoyl chloride in the presence of a Lewis acid as follows:

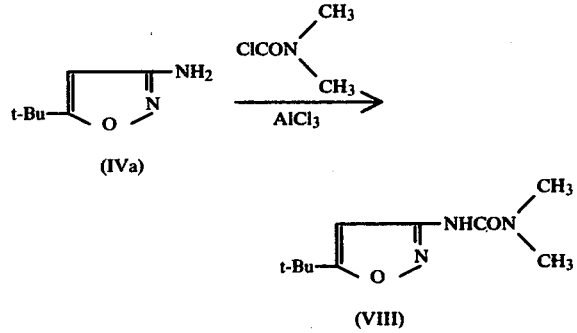

(IVa)

(VIII)

(wherein t-Bu is tertiary butyl).

The present invention is further described and illustrated in detail by way of the following Examples.

EXAMPLE 1

To a suspension of cyanopinacolone (75.102 g) in a mixture of anhydrous toluene (150 ml) and anhydrous methanol (26.7 ml) is introduced gaseous hydrogen chloride (26.3 g) with cooling at 5° to 10° C. and stirring, and the whole mixture is allowed to stand at 10° to 12° C. for 23 hours. To the reaction mixture is dropwise added anhydrous methanol (750 ml), then triethylamine (185.178 g) with cooling and stirring to make a complete solution. The reaction mixture is treated with hydroxylamine sulfate (51.704 g) and stirred at 50° C. for 2 hours. Then, conc. hydrochloric acid (112.629 g) is dropwise added to the mixture, which is stirred at 50° C. for 1 hour. After evaporating the solvent under reduced pressure from the reaction mixture, the residue is made alkaline with 48% aqueous sodium hydroxide with cooling, and the aqueous solution is shaken with toluene. The organic layer is washed with water, subjected to azeotropic distillation under atmospheric pressure, and evaporated to dryness to remove the solvent, whereby 3-amino-5-t-butylisoxazole (79.480 g) is obtained. Melting point is 106° to 109° C. Yield is 94.5%.

EXAMPLE 2

(1) To a suspension of cyanopinacolone (25.034 g) in anhydrous toluene (50 ml) and anhydrous methanol (8.9 ml) is added gaseous hydrogen chloride (9.9 g) with cooling and stirring at 5° to 10° C., and the whole mixture is allowed to stand at 5° to 10° C. for 25 hours. The reaction mixture is mixed with n-hexane and the precipitated hydrochloride is filtered and washed with ethyl acetate to give methyl 4,4-dimethyl-3-oxopentanimidate hydrochloride (37.746 g) as crystals melting at 104° to 104.5° C. (decomp.). Yield is 97.5%.

(2) To a solution of sodium hydrogen carbonate (2.17 g) in water (40 ml) is added methylene chloride (50 ml), and then with ice cooling and stirring the above obtained methyl 4,4-dimethyl-3-oxopentanimidate hydrochloride is added thereto. At once, two layers separate, the organic layer is decanted, washed with water, dried over anhydrous sodium sulfate, and the solvent is evaporated off under reduced pressure to give crystalline residue. This residue is triturated with n-hexane and filtered to give 4,4-dimethyl-1-methoxy-3-oxo-1-pentenylamine (3.97 g) as crystals melting at 79° to 79.5° C. Yield is 98%.

(3) 4,4-Dimethyl-1-methoxy-3-oxo-1-pentenylamine (1.572 g), anhydrous methanol (12 ml), and triethylamine (2.052 g) are mixed together to afford a clear solution. Hydroxylamine hydrochloride (0.902 g) is added with stirring to the solution, which is heated at 50° to 52° C. for 2 hours. The resultant mixture is mixed with conc. hydrochloric acid (2.15 ml), stirred at 50° to 52° C. for 1 to 1.5 hours, and the methanol is evaporated off under atmospheric pressure. The residue is made alkaline with 40% aqueous sodium hydroxide and the solution is extracted with chloroform. The organic layer is washed with a small amount of water, dried over anhydrous sodium sulfate, and the solvent is evaporated to give a crystalline residue (1.361 g). This crude product is recrystallized from benzene to give 3-amino-5-t-butylisoxazole as colorless crystals melting at 111° to 112° C. Yield is 97%.

EXAMPLE 3

Using N-methylmorpholine (1.52 g) instead of triethylamine, the reaction is effected as in Example 2(3) above, whereby 3-amino-5-t-butylisoxazole (1.21 g) is obtained. Yield is 86.0%.

EXAMPLE 4

(1) Using cyanopinacolone, the reaction is effected as in Example 2(1), whereby methyl 4,4-dimethyl-3-oxopentanimidate hydrochloride is obtained. Yield is 97.5%.

(2) To a suspension of above obtained methyl 4,4-dimethyl-3-oxopentanimidate hydrochloride (19.40 g) in anhydrous methanol (120 ml), triethylamine (25.3 g) is added dropwise with cooling below 15° C. and stirring. The resultant mixture is mixed with hydroxylamine sulfate (9.02 g) and stirred at about 50° C. for 2 hours. Then, conc. hydrochloric acid (26.1 g) is dropwise added to the mixture, which is stirred at about 50° C. for 1 hour and evaporated under atmospheric pressure to remove the solvent. The residue is made alkaline with aqueous 40% sodium hydroxide and the resulting solution is shaken with chloroform. The organic layer is washed with water, dried over anhydrous sodium sulfate, and then the chloroform is evaporated to give 3-amino-5-t-butylisoxazole (13.359 g) as crystals melting at 107° to 109° C. Yield is 95.4%.

EXAMPLES 5-8

Using the starting materials cyanopinacolone (Ia) and II, the reactions are effected as in Example 4 to give the 3-amino-5-t-butylisoxazole (IVa) via the corresponding iminium salt (III) as shown below.

Table I

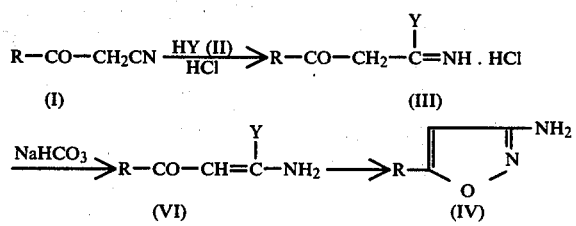

| Ex. No. | II Y | III m.p. (°C.) | III Yield (%) | IVa Yield (%) |
|---|---|---|---|---|
| 5 | EtO | 119–120 (d) | 97.0 | 94 |
| 6 | i-PrO | 122–123 (d) | 95.0 | 92 |
| 7 | i-BuO | 129–130 (d) | 95.0 | 91 |
| 8 | i-PrS | 135–137 | 92.0 | 90 |

(Note) The abbreviations in Table I have the following significance.
Et (ethyl),
Bu (butyl),
Pr (propyl),
d (decomp.),
i (iso)

EXAMPLES 9-11

Using the starting materials (I) and (II), reactions are effected as in Example 2, whereby the objective compounds (IV) are obtained via the corresponding iminium salts (III) and enaminoketones (VI) as shown below.

$$R-CO-CH_2CN \xrightarrow[HCl]{HY\ (II)} R-CO-CH_2-\overset{Y}{\underset{|}{C}}=NH \cdot HCl$$

$$\xrightarrow{NaHCO_3} R-CO-CH=\overset{Y}{\underset{|}{C}}-NH_2 \longrightarrow R-\underset{O}{\overset{}{\diagdown}}\underset{N}{\overset{}{\diagup}}-NH_2$$

(I)  (III)  (VI)  (IV)

Table II

| Ex. No. | I R | II Y | III m.p. (°C.) | III Yield (%) | VI m.p. (°C.) | VI Yield (%) | IV m.p. (°C.) | IV Yield (%) |
|---|---|---|---|---|---|---|---|---|
| 9 | t-Bu | EtO | 119–120(d) | 97 | 59–60.5 | 98 | 111–112 | 97 |
| 10 | i-Pr | MeO | 99–100(d) | 96 | 107–108 | 98 | 71.5–72.5 | 88 |
| 11 | Cl-⟨phenyl⟩ | MeO | 145–148(d) | 85 | 110–111 | 99 | 144–145 | 81 |

(Note) The abbreviations in Table II have the same significance as in Table I.

What is claimed is:

1. A process for the production of a 3-aminoisoxazole of the formula:

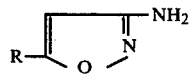

wherein R is $C_1$–$C_6$ alkyl, phenyl or halophenyl, which process comprises
reacting a β-ketonitrile of the formula:

R—CO—CH$_2$CN wherein R is as defined above, with a compound of the formula:

HY wherein Y is C$_1$-C$_6$ alkoxy or C$_1$-C$_6$ alkylthio, in the presence of an acid selected from the group consisting of hydrogen chloride, hydrogen bromide and sulfuric acid in a solvent, with cooling below room temperature, to give an iminium salt of the formula:

$$RCOCH_2-\underset{\underset{Y}{|}}{C}=NH \cdot HX$$

wherein X is the residue of said acid and R and Y are each as defined above, reacting the iminium salt with hydroxylamine in an inert solvent under a basic condition at a temperature below 100° C., and treating the resultant product with an acid selected from the group consisting of hydrochloric acid, sulfuric acid and acetic acid at a temperature below 100° C.

2. A process according to claim 1, wherein the β-ketonitrile is cyanopinacolone.

3. A process according to claim 1, wherein the acid, whose residue is x, is hydrogen chloride.

4. A process according to claim 2, wherein the 3 aminoisoxazole product is 3-amino-5-t-butylisoxazole.

* * * * *